(12) United States Patent
Hahn et al.

(10) Patent No.: US 7,157,053 B2
(45) Date of Patent: Jan. 2, 2007

(54) ABSORBANCE DETECTION SYSTEM FOR LAB-ON-A-CHIP

(75) Inventors: Jong Hoon Hahn, Pohang (KR); Kyung Won Ro, Pohang (KR); Bong Chu Shim, Seoul (KR); Kwanseop Lim, Pohang (KR)

(73) Assignee: Pohang University of Science and Technology Foundation, Pohang (KR)

( * ) Notice: Subject to any disclaimer, the term of this patent is extended or adjusted under 35 U.S.C. 154(b) by 480 days.

(21) Appl. No.: 10/196,946

(22) Filed: Jul. 18, 2002

(65) Prior Publication Data

US 2003/0017079 A1 Jan. 23, 2003

(30) Foreign Application Priority Data

Jul. 18, 2001 (KR) .............................. 2001-43106

(51) Int. Cl.
*G01N 31/00* (2006.01)

(52) U.S. Cl. ...................... 422/82.69; 422/55; 422/57; 422/68.1; 422/82.05; 422/82.06; 422/50

(58) Field of Classification Search .................. 422/50, 422/55, 57, 68.1, 82.05, 82.06, 82.11
See application file for complete search history.

(56) References Cited

U.S. PATENT DOCUMENTS 6,100,541 A * 8/2000 Nagle et al. ................ 250/573

* cited by examiner

*Primary Examiner*—Jill Warden
*Assistant Examiner*—Sam P. Siefke
(74) *Attorney, Agent, or Firm*—Leydig, Voit & Mayer, Ltd.

(57) ABSTRACT

A high-efficiency, high-sensitivity absorbance detection system in a lab-on-a-chip is provided. The absorbance detection system includes detection cells having an optical pathlength ten times and/or much longer than the width of a separation channel to improve detection sensitivity, lens structures for collimating light in the detection cells, and slit structures for preventing scattered light from entering detectors. The detection cells, the lens structures, and the slit structures of the absorbance detection system are fabricated and integrated in a lab-on-a-chip. The absorbance detection system exhibits excellent absorption efficiency, detection limit, and linearity, compared to existing absorbance detection systems, and can be applied for the detection of a variety of samples. The absorbance detection system does not need labeling of the samples which saves time and costs. The absorbance detection system can be used effectively in detecting trace compounds with a high sensitivity. The absorbance detection system in a lab-on-a-chip can be used with wider applications to a variety of samples in diverse research fields, such as the drug screening field dealing with simultaneous synthesis and identification of a number of compounds based on combinatorial chemistry, the life sciences field handling trace bioactive materials such as enzymes, proteins, and amino acids, and the environmental research field which needs rapid field monitoring of contaminants.

15 Claims, 8 Drawing Sheets

ABSORBANCE DETECTION SYSTEM FOR LAB-ON-A-CHIP

BACKGROUND OF THE INVENTION

1. Field of the Invention

The present invention relates to an absorbance detection system in a lab-on-a-chip, and more particularly, to a high-efficiency, high-sensitivity absorbance detection system in which detection cells with long optical path lengths for higher detection sensitivity, micro-lenses for collimating light into the detection cells, and slits for preventing scattered light from entering detectors are fabricated and integrated in a lab-on-a-chip.

The present invention of an absorbance detection system in a lab-on-a-chip is capable of solving the problems of conventional absorbance detection systems in lab-on-a-chips and produces a 10 times greater detection sensitivity.

The invented detection system can utilize liquid- or solid-state waveguides or micro-light sources (lamp or laser) as well as optical fibers for light radiation.

The present invention has additional collimators including micro-lenses and slits arranged close to detection cells so that effective absorbance detection can be achieved using the detection cells with the 50 μm or greater optical pathlengths.

The present invention of an absorbance detection system in a lab-on-a-chip has collimators including micro-lenses for collimating divergent light from optical fibers and transmitting the collimated light to detection cells. Slits are built-in to prevent light that does not pass through the detection cell or scattered light from entering detectors so that detection sensitivity can be improved markedly with increased optical pathlength of the detection cell.

2. Description of the Related Art

A variety of analytical instruments such as capillary electrophoresis (CE), liquid chromatography, and gas chromatography are used to separate and analyze mixed compounds. In particular, CE and liquid chromatography have wide applications in conjunction with a variety of available detection methods, such as absorbance detection, fluorescence detection, electrochemical detection and others. The fluorescence detection method advantageously has a high detection sensitivity but needs fluorescence labels to be coupled to samples because self-luminescent substances rarely exist. The electrochemical method also has a high detection sensitivity but its application is limited to specific compounds. Whereas, the absorbance detection method can be applied to a wide range of analytes and does not need labeling of analytes for detection, and thus it has been the most popular detection method.

In the absorbance detection method based on Beer's law, the absorbance of a sample is proportional to the distance light passes through the sample, i.e., the optical pathlength, which is expressed by:

$$A = \epsilon \times b \times C \qquad (1)$$

where A is absorbance, $\epsilon$ is the molar extinction coefficient (L/mol·cm), b is the optical pathlength (cm), C is the molar concentration of the sample (mol/L).

Sensitivity of the absorption detection is usually poor in CE. This is because the capillary used for CE has a small inner diameter of 50–100 μm, and thus the optical pathlength is very short. In addition, because the capillary has a circular cross-section, a portion of light passes through the capillary, and thus the actual pathlength is smaller than the inner diameter of the capillary.

In an attempt to increase the sensitivity of absorbance detection in CE, detection cells with an extended optical pathlength have been developed. Typically, the use of a capillary having a rectangular cross-section or a U-shaped or Z-shaped detection cell has been suggested to increase the optical pathlength by 10–50 times the inner diameter of a common capillary.

In a lab-on-a-chip based CE system, the depth of microchannels formed in a glass plate or plastic plate is as small as 10–30 μm, and thus the absorbance detection sensitivity in the microchip system is worse than that in CE. For this reason, an attempt to increase detection sensitivity by applying a U-shaped detection cell in a lab-on-a-chip system has been made. In this approach, optical fibers are arranged in front of and behind the detection cell, and light is radiated into the detection cell through an optical fiber and collected by another optical fiber for detection.

Lab-on-a-chip systems for chemical/biological analysis will be described briefly. Lab-on-a-chip systems fabricated by a micro-machining technique such as a photolithography technique used in the manufacture of semiconductor devices are referred to as chemical microprocessors including a variety of components (for sample pretreatment, injection, reaction, separation and detection) integrated in a glass, silicon, or plastic substrate of an area of several square centimeters. These lab-on-a-chip systems advantageously enable high-speed, high-efficiency, high-cost automated chemical/biological analysis to be carried out just on the one device.

In most lab-on-a-chip based analytical systems, migration and separation of a sample are performed by electroosmotic flow induced by the application of voltages to both ends of a microchannel filled with a sample solution. The microfluidics in a microchip can be controlled by applying high voltages and thus eliminating the use of a mechanical pump or valve. This has enabled the microchip to be fabricated to much smaller sizes than other commercially available analytical systems and at relatively low costs. In addition, a series of sample injection, migration, reaction, separation and detection processes can be performed continuously in a single lab-on-a-chip.

Although the lab-on-a-chip-based analytical systems described above are advantageous in that the consumption of sample and reagents is reduced and the analysis can be performed within a short period of time, they cannot be applied to the analysis of a variety of samples due to limited detection methods. So, fluorescence detection and electrochemical detection methods are commonly used for detection in a lab-on-a-chip. To compensate for the drawback of the lab-on-a-chip-based analytical systems and to extend its applications, a glass based lab-on-a-chip integrated with an absorption detection system using optical fibers was developed. In this system, a single mode optical fiber having a small numerical aperture and a small core diameter was used in order that almost all of the radiated light passes through a U-shaped detection cell. Light passed through a single mode optical fiber diverges conically at a predetermined angle. The diameter (w) of light from the single mode optical fiber is calculated by:

$$w = d \times (0.65 + 1.619/V^{1.5} + 2.879/V^6) \qquad (2)$$

where d is the diameter of the optical fiber, and $V = d \times \pi \times NA/\lambda$ where NA is the numerical aperture of the optical fiber, and $\lambda$ is the wavelength of radiated light.

With this type of a conventional absorption detection system in a lab-on-a-chip, an optical fiber having a core diameter of 3 µm, a cladding diameter of 125 µm, and an NA of 0.1 is used, and 488-nm light is radiated from an argon ion laser. The diameter of light from this optical fiber, which can be calculated by formula (2) above, is 3.93 µm. Here, the divergence angle (θ) of light is calculated by:

$$\theta = \arcsin(NA/n) \quad (3)$$

where n is the refractive index of a medium through which light transmits (n=1.33 for water, n=1.52 for glass). The diameter (w') of divergent light at a distance (X) from the medium is calculated by:

$$w' = w + 2X \tan\theta \quad (4)$$

As an example, assuming that light from a single mode optical fiber passes through a detection cell filled with water and having a length of 150 µm, the divergent light from the detection cell, which can be calculated by the formulae above, has a diameter of about 27 µm. If the detection cell has a length of 500 µm, the divergent light from the detection cell has a diameter of about 80 µm. Therefore, when designing a U-shaped detection cell having a depth of 25 µm and a width of 50 µm for a lab-on-a-chip using a single mode optical fiber, the length of the U-shaped detection cell is determined to be no larger than 150 µm to allow almost all the light radiated through the single mode optical fiber to pass through the U-shaped detection cell. As a result, the conventional absorbance detection system in a lab-on-a-chip showed an increase in detection sensitivity by only 3–4 times of that of a detection method in an non-extended detection cell.

In addition, because the conventional absorbance detection system in a lab-on-a-chip is fabricated in glass, it is difficult to fabricate, is time consuming and has low reproducibility. Also, the detection cell (channel) of the absorbance detection system has a circular cross-section and thus generates a serious light scattering problem.

SUMMARY OF THE INVENTION

To solve the above problems, it is an object of the present invention to provide a high-efficiency, high-sensitivity absorbance detection system in a lab-on-a-chip in which detection cells with long optical pathlengths for higher detection sensitivity, micro-lenses for collimating light into the detection cells, and slits for preventing scattered light from entering the detectors are fabricated and integrated in the lab-on-a-chip.

Another object of the present invention is to provide an absorbance detection system in a plastic lab-on-a-chip capable of solving the problems of conventional absorbance detection systems in lab-on-a-chips and produces a 10 times greater detection sensitivity.

Still another object of the present invention is to provide an absorbance detection system in a lab-on-a-chip in which liquid- or solid-state waveguides or micro-light sources (lamp or laser) as well as optical fibers can be used for light radiation.

Yet still another object of the present invention is to provide an absorbance detection system in a lab-on-a-chip in which an additional collimator, including micro-lenses and slits, are arranged close to detection cells so that effective absorbance detection can be achieved using the detection cells with optical pathlengths of 50 µm or longer.

The present invention also aims to provide an absorbance detection system in a lab-on-a-chip in which collimators, including micro-lenses for collimating divergent light from optical fibers and transmitting the collimated light into detection cells and slits for preventing light that does not pass through the detection cells or scattered light from entering detectors, are built-in so that detection sensitivity can be improved markedly with the increased optical pathlengths of the detection cells.

In achieving the objects of the present invention, the fabrication of a lab-on-a-chip is carried out to build an absorbance detection system comprising: detection cells having optical pathlengths of 50 µm–5 mm; lens structures for collimating and transmitting light to the detection cells; and slit structures for preventing scattered light from entering detectors.

In one embodiment, the lens structures and the slit structures may form collimators to transmit collimated light to the detection cells.

BRIEF DESCRIPTION OF THE DRAWINGS

The above objects and advantages of the present invention will become more apparent by describing in detail preferred embodiments thereof with reference to the attached drawings in which.

DETAILED DESCRIPTION OF THE INVENTION

Preferred embodiments of an absorbance detection system for a lab-on-a-chip according to the present invention will be described in detail with reference to the appended drawings. Description of the prior art or the unnecessary structure of the present invention that makes the subject matter obscure will be omitted. The terms used in the following description are defined on the basis of functions, and thus it will be appreciated by those skilled in the art that the terms may be changed appropriately based on users' or operators' intentions and practices without departing from the meaning intended in the following description.

Figure 1A:
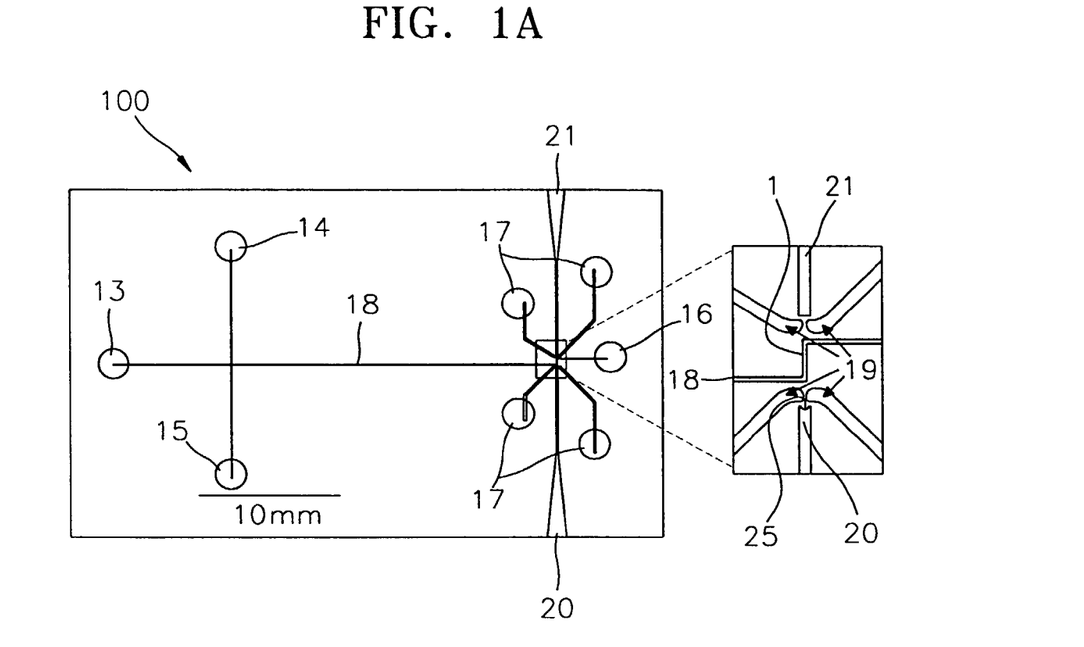
FIGS. 1A and 1B are plan views of preferred embodiments of an absorbance detection system in a lab-on-a-chip according to the present invention.
Figure 1B:
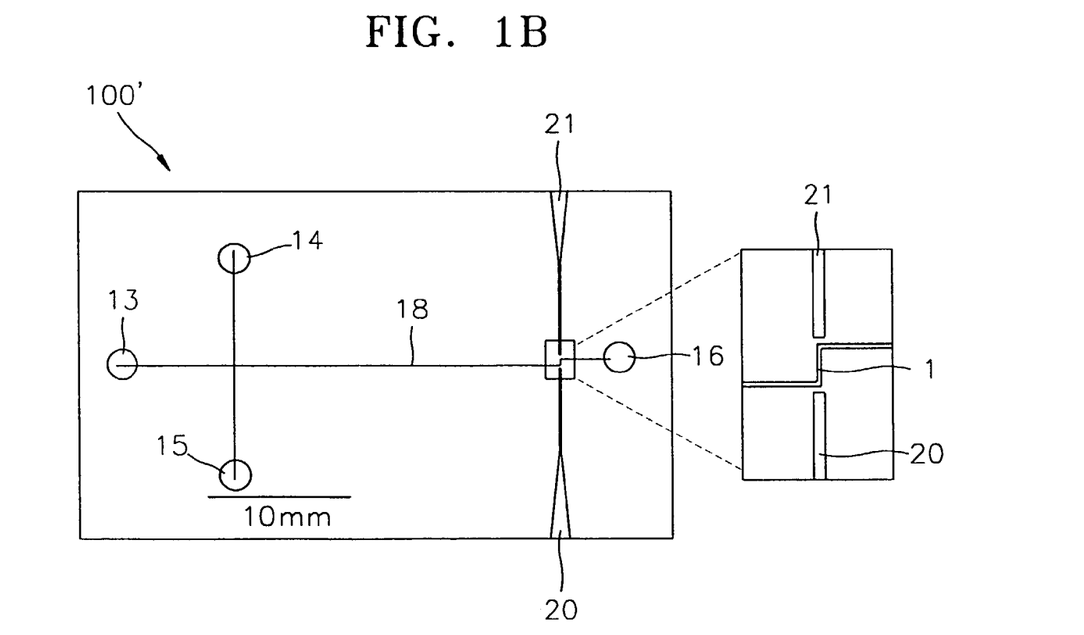

FIGS. 1A and 1B show preferred embodiments of an absorbance detection system in a "lab-on-a-chip" according to the present invention. In particular, FIG. 1A shows a high-performance absorbance detection system 100 built in a lab-on-a-chip having a collimator, and FIG. 1B shows an absorbance detection system 100' built in a lab-on-a-chip that does not have a collimator. In this specification, the collimator is defined as comprising a lens 25 and slits (channels) 19 and collimates light for an absorbance detection cell (hereinafter, "detection cell") 1. The collimator is not designated by a particular reference numeral in the following description.

In FIGS. 1A and 1B, reference numeral 13 denotes a sample reservoir, reference numeral 14 denotes a buffer reservoir, reference numeral 15 denotes a sample waste reservoir, reference numeral 16 denotes a buffer waste reservoir, and reference numeral 17 denotes an ink reservoir for containing ink used to fill the slits 19. Reference numeral 18 denotes a separation channel having a width of 5 μm to 1 mm. The width of the separation channel 18 is determined depending on the application field.

In the absorbance detection systems 100 and 100' in the lab-on-a-chip shown in FIGS. 1A and 1B, both the detection cells 1 have the same optical pathlength, of 50 μm to 5 mm, which is determined depending on the application field. The detection cells 1 are connected to the respective separation channels 18.

In FIG. 1A, an element denoted by reference numeral 25 and located near the end of a source fiber channel 20 is a micro-lens having a diameter of 5 μm to 1 mm, which collimates light. A convex lens, a convex-concave compound lens, or a gradient-index(GRIN) lens can be used as the micro-lens 25.

In designating the constituent elements of the absorbance detection system according to the present invention, the terms including "channel", for example, "optical fiber channel" or "slit channel", define constructions for corresponding functional elements, i.e., for "optical fiber" or "slit". Therefore, the terms "optical fiber channel" and "optical fiber" or "slit channel" and "slit" can be used as having the same meaning through the specification.

Reference numeral 19 denotes a slit (channel) for preventing scattered light from entering a detection cell (not shown) and is filled with a light absorbing material such as black ink for use. Reference numeral 20 denotes a source fiber channel having a width of 5 μm to 1 mm. Reference numeral 21 denotes a collection fiber channel, which receives light from the detection cell 1 and transmits the same to a detector (see FIG. 5). In the source and collection fiber channels 20 and 21, the outer end of each channel is formed to be wider than the inner end thereof for easy insertion of an optical fiber into the channel.

Figure 3:
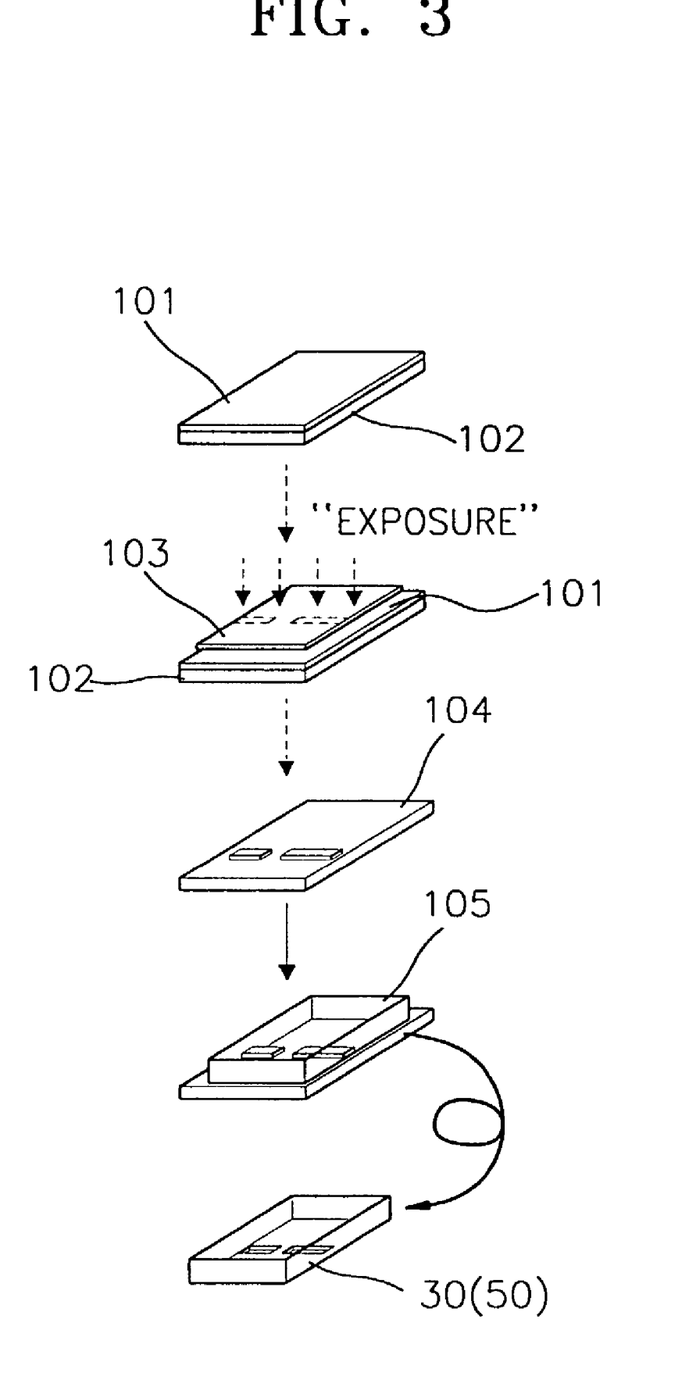
FIG. 3 illustrates the fabrication process of top and bottom plates for the absorbance detection system according to the present invention.
Figure 4:
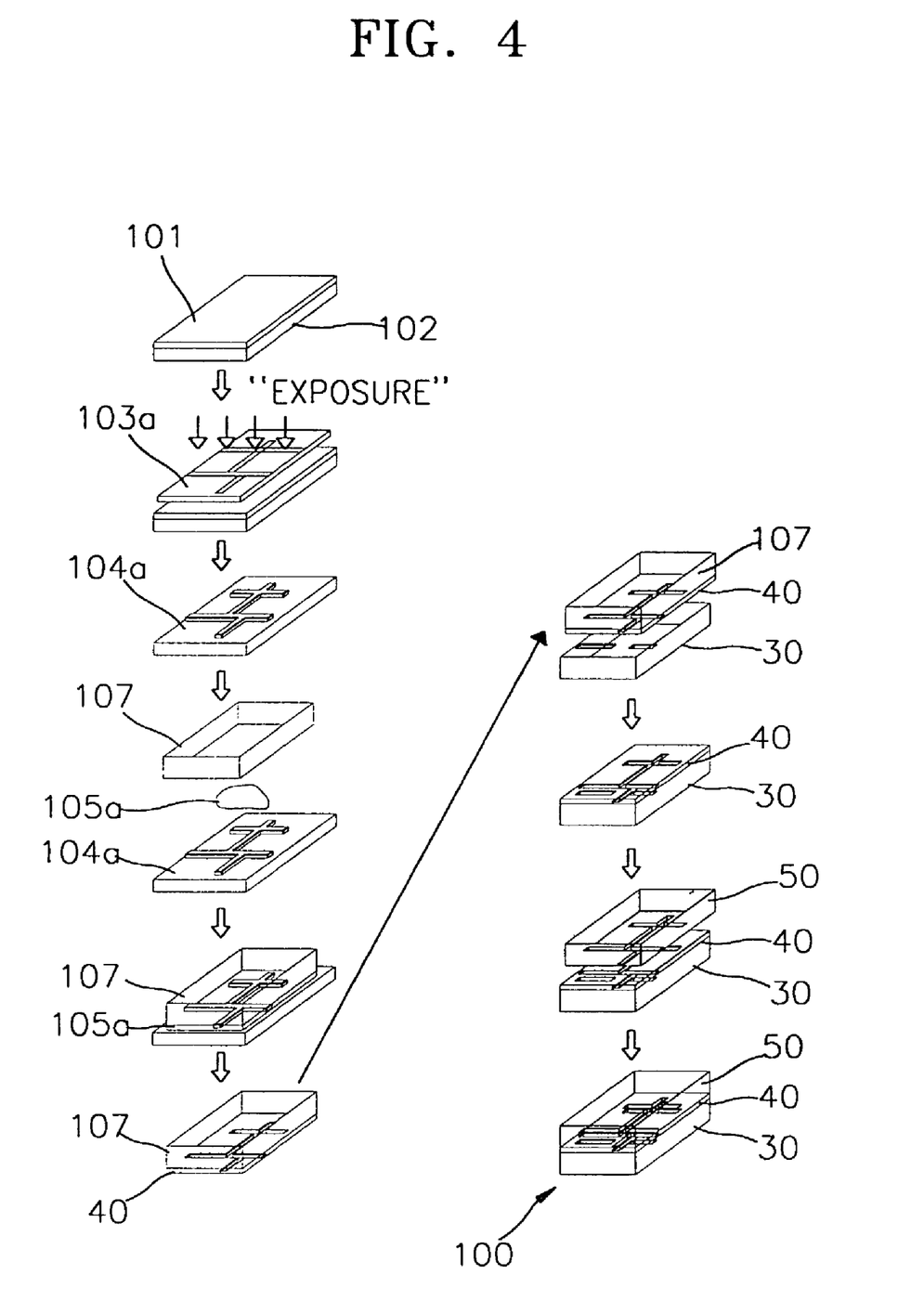
FIG. 4 illustrates the fabrication process of a membrane plate for the absorbance detection system according to the present invention and the bonding of the membrane plate to the top and bottom plates.

Fabrication of the absorbance detection systems 100 and 100' in each of the lab-on-a-chip shown in FIGS. 1A and 1B will be described with reference to FIGS. 2 through 4.

An absorbance detection system in a lab-on-a-chip in which fiber channels and 3-dimensional slits 19 are arranged in front of and behind a detection cell 1 is fabricated as a three-layered structure using three photomasks. FIG. 2 is a magnified perspective view of the absorbance detection system 100 in a lab-on-a-chip.

Figure 2:
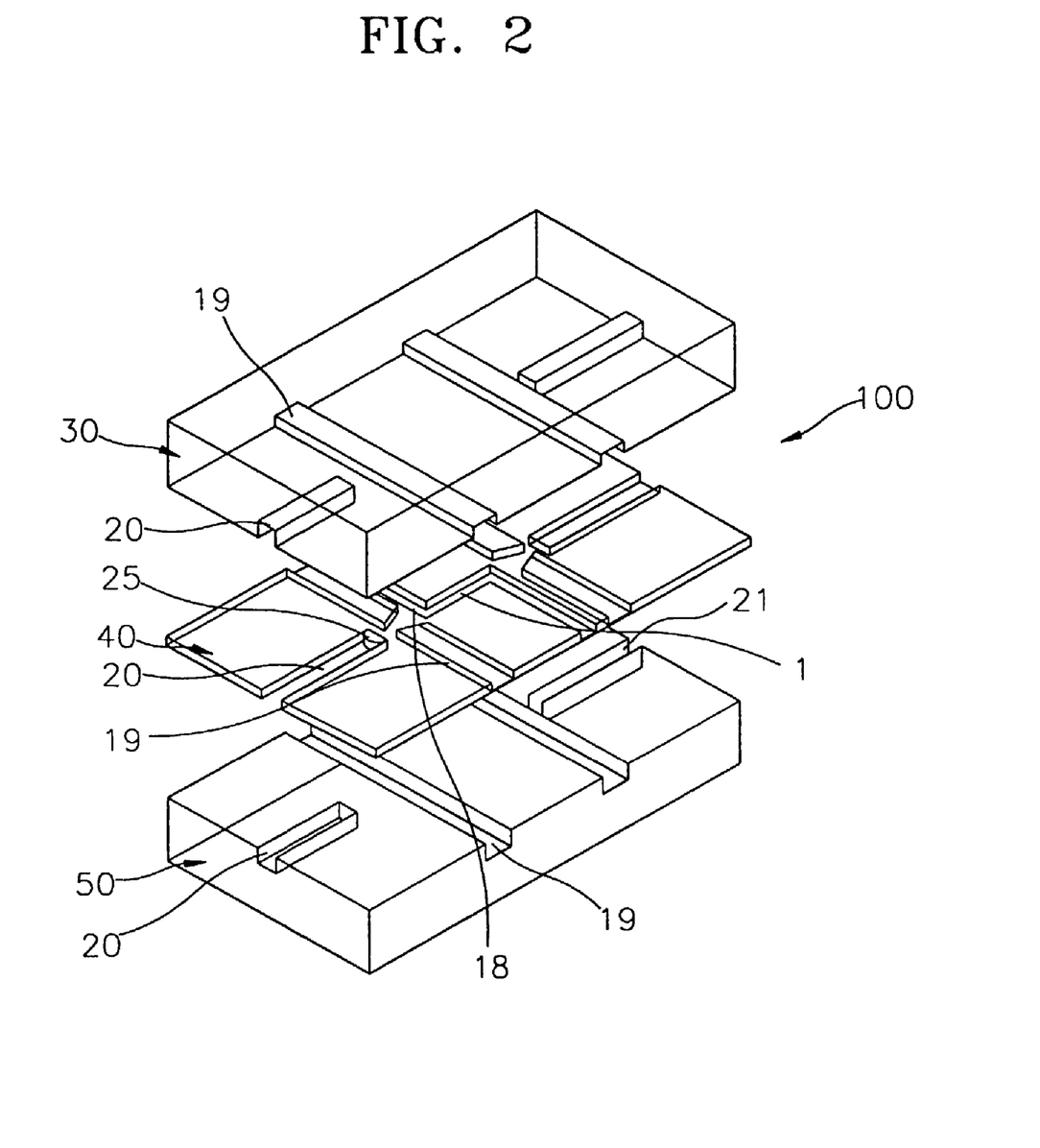
FIG. 2 is a magnified perspective view showing each layer of the absorbance detection system according to the present invention.

Referring to FIG. 2, the source fiber channel 20, the collection fiber channel 21, and the slit channel 19, each having a depth of 5 μm to 1 mm, are formed in an top plate 30. A membrane plate 40 as thin as 5 μm to 1 mm has the separation channel 18, the detection cell 1, the optical fiber channel 20, and the slit channel 19, which are formed through the membrane plate 40. In the membrane plate 40, the microlens 25, preferably, a micro-planoconvex lens, is formed on one end of the source fiber channel 22.

As in the top plate 30, the source fiber channel 20, the collection fiber channel 21, and the slit channel 19, each having a depth of 5 μm–1 mm, are formed in a bottom plate 50. Here, the width of the slit channels 19 in the top plate 30 and the bottom plate 50 are formed to be 5–10 times wider than that of the detection cell 1. In the membrane plate 40, each of the slit channels 19 are divided with a separation gap corresponding to the width of the detection cell 1.

Preferably, the top, membrane, and bottom plates 30, 40, and 50 for the lab-on-a-chip are formed in plastics including polydimethylsiloxane (PDMS), polymethylmethacrylate (PMMA), polycarbonate (PC), polyethylene (PE), polypropylene (PP), and polystyrene (PS). In forming such microchannels and structures in the top, membrane, and bottom plates 30, 40, and 50, a molding technique using a template shaping a molten plastic by hardening, a hot embossing technique in which a planar substrate is hot pressed with a template, or other processing techniques, such as casting, mechanical machining, and laser machining, using a mechanical tool or a light or heat source can be applied.

As an example, a method for manufacturing the top, membrane, and bottom plates 30, 40, and 50 using PDMS by molding will be described below.

The top and bottom plates 30 and 50 with channels are fabricated as follows. Referring to FIG. 3, a negative-type photoresist 101, SU-8, is coated on a silicon wafer 102 to a thickness of 5 μm to 1 mm, and a photomask 103 having a pattern is placed on the silicon wafer 102 and exposed to ultraviolet (UV) light. The UV-exposed negative-type photoresist 101 is developed in a developer solution to form a positive mold 104 with a pattern having a height of 40 to 250 μm. PDMS 105 is spread over the positive mold 104 and peeled off after cross-linking, resulting in the top plate 30 or bottom plate 50 having a negative pattern for a lap-on-a-chip.

Processes for fabricating the membrane plate 40 for the absorbance detection system 100 and bonding the membrane plate 40 to the top and bottom plates 30 and 50 will be described with reference to FIG. 4.

As described with reference to FIG. 3, a negative-type photoresist 101 is coated on a silicon wafer 102 to a thickness of 5 μm to 1 mm, and a photomask 103a having a desired pattern specified for the membrane plate 40 is placed on the silicon wafer 102 and exposed to UV light. The UV-exposed negative-type photoresist 101 is developed to form a positive mold 104a with a pattern having a height of 5 μm–1 mm. PDMS 105a is spread over the positive mold 104a and then pressed with a flat PDMS plate 107 to transfer the positive pattern of the positive mold 104 on the spread PDMS 105a by cross-linking so that the membrane plate 40 is formed. The PDMS plate 107 is oxidized by corona discharge using a Tesla coil (not shown) and silanized so that the membrane plate 40 formed of PDMS can be separated easily from the PDMS plate 107.

After separating the membrane plate 40 and the PDMS plate 107 from the silicon wafer 102, on which the positive mold 104a is formed, the membrane plate 40 and the top plate 30 are subjected to surface treatment using the Tesla coil and bonded to each other after pattern alignment. It will be appreciated by those skilled in the art that surface treatment performed on PDMS plates using a Tesla coil before bonding can be applied to glass plates or silicon wafers.

After separating the PDMS plate 107 from the membrane plate 40, reservoir holes for the reservoirs 13 through 17 shown in FIG. 1 are punched in the assembly of the membrane plate 20 and the top plate 30. Next, the other surface of the membrane plate 40 and the bottom plate 50 are subjected to surface treatment, and the bottom plate 50 is bonded to the membrane plate 40 after alignment, resulting in the absorbance detection system 100 in a lab-on-a-chip.

Figure 5:
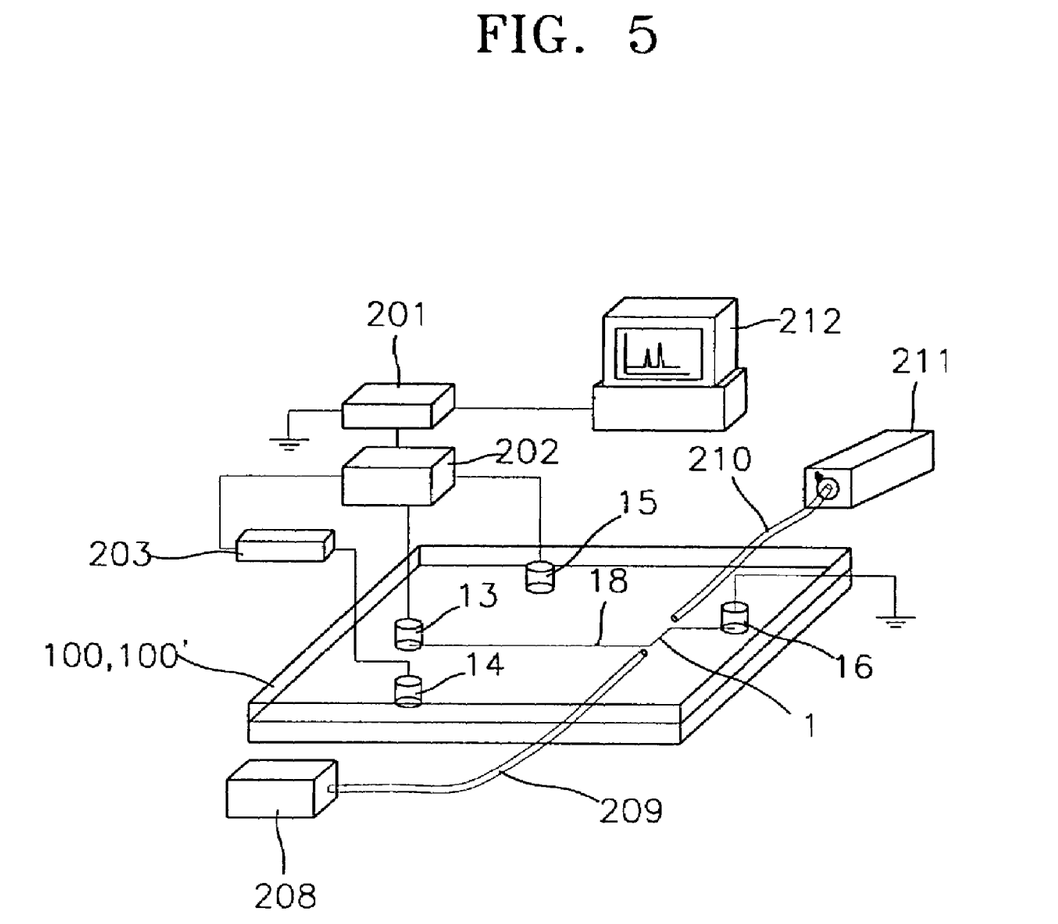
FIG. 5 shows an experimental setup for absorbance detection in a lab-on-a-chip according to the present invention.

Referring to FIG. 5, 200 μL pipette tips cut to appropriate sizes are inserted into the reservoir holes in the absorbance detection system 100. A source fiber 209 having a core diameter of 1 μm to 1 mm and a cladding diameter of 2 μm to 2 mm is inserted into the source fiber channel 20 (see FIG. 1). A collection fiber 210 having a core diameter of 1 μm to 1 mm and a cladding diameter of 2 μm to 2 mm is inserted into the collection fiber channel 21 (see FIG. 1). When a collimator is arranged near the detection cell 1, as shown in FIG. 1A, the source fiber 209 must be positioned at the focal length of the micro-planoconvex lens 25 (see FIG. 2) to emit collimated light to the detection cell 1. Finally, a material capable of adsorbing scattered light, for example, black ink, is put into the reservoir 17 (see FIG. 1) and fills the slit channels 19.

The structure and operation of a separation and absorbance detection system using an absorbance detection system in a lab-on-a-chip according to the present invention will be described with reference FIG. 5.

A preferred embodiment of a separation and absorbance detection system for the lab-on-a-chip 100(100') is shown in FIG. 5. Sample migration, injection, and separation in the lab-on-a-chip 100(100') are achieved by electroosmotic flow. To this end, a high-voltage power supply 201, a voltage divider 202, and a high-voltage relay 203 are used. Sample injection is performed by a gate injection method. In this case, voltages applied to the sample reservoir 13, the buffer reservoir 14, and the sample waste reservoir 15 are adjusted by the voltage divider 202. Before injection, a 0.1 to 10 kV is applied to the sample reservoir 13, a voltage 0.3 to 0.9 times the voltage provided to the sample reservoir 13 is applied to the buffer reservoir 14, and a voltage 0 to 0.9 times the voltage provided to the sample reservoir 13 is applied to the sample waste reservoir 15. The buffer waste reservoir 16 is connected to ground.

For sample injection, the voltage applied to the buffer reservoir 14 is floated for a predetermined time period, e.g. 0.01 to 100 seconds, by the high-voltage relay 203 and then reapplied. The injected sample is separated while passing through the separation channel 18 and then detected by absorbance detection using a UV lamp, such as deuterium, mercury, tungsten, or xenon lamp, or a kind of laser along with an optical fiber. In the present embodiment, an argon ion laser 208 emitting a wavelength of 488 nm is used as a light source. Light from the argon ion laser 208 is transmitted to the detection cell 1 through the source fiber 109, and the light from the detection cell 1 is transmitted to the detector 211 through the collection fiber 210. The detector (photo diode or photo multiplier tube (PMT)) 211 measures the intensity of the collected light. A computer 212 controls the high-voltage power supply 201 and the high-voltage relay 203 and records and stores the signals output from the detector 211.

A light path in the detection cells in different absorbance detection systems will be comparatively described with reference to FIGS. 6 through 9. In FIGS. 6 through 9, reference numeral ① denotes a detection cell, reference numeral ② denotes a source fiber, reference numeral ②' denotes a collection fiber, reference numeral ③ denotes a planoconvex lens, and reference numeral ④ denotes a slit.

Figure 6:
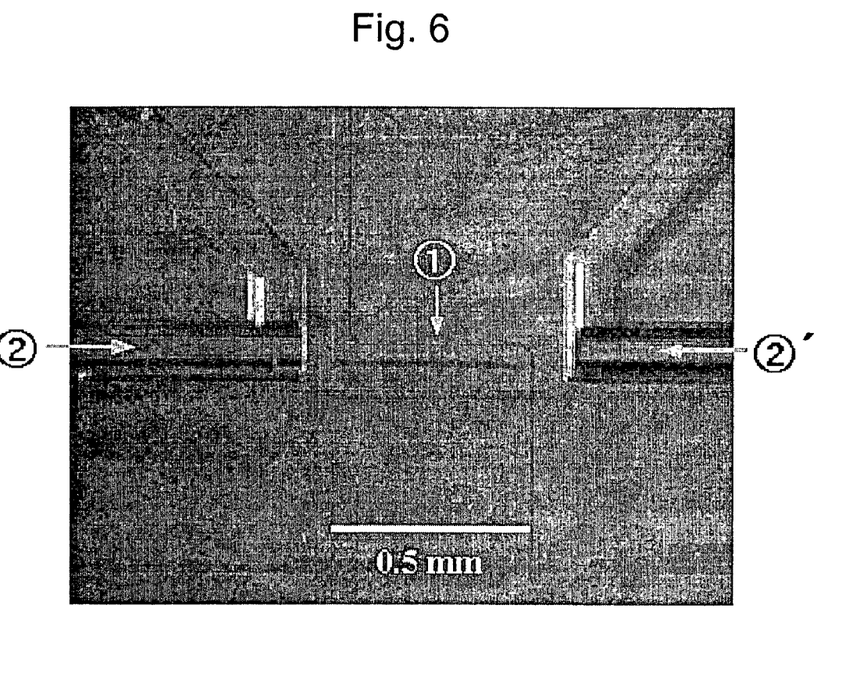
FIG. 6 is a photograph of an absorbance detection system without a collimator near the detection cell according to the present invention.
Figure 7:
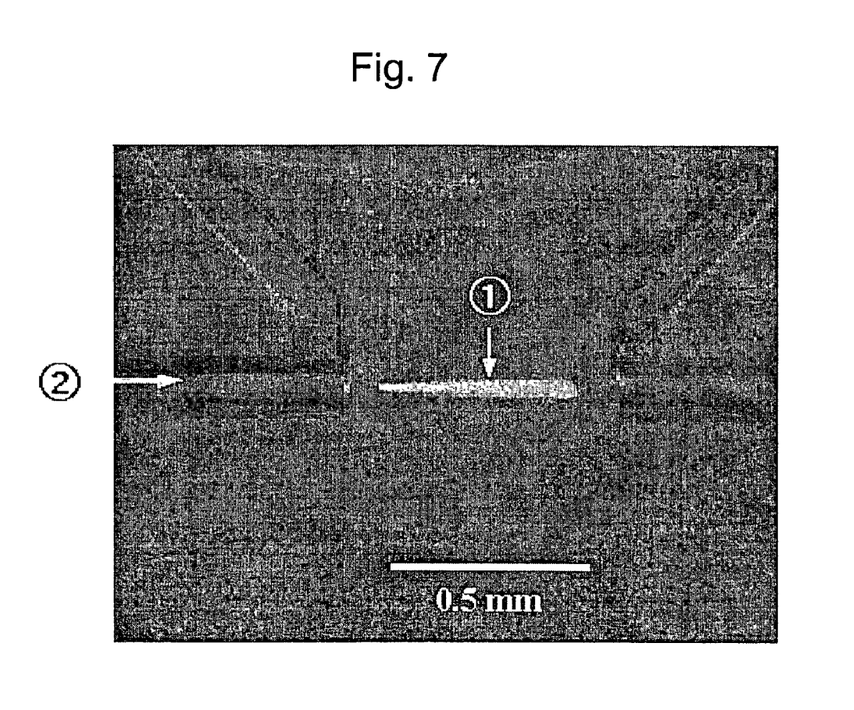
FIG. 7 is a photograph showing light passing through the detection cell of the absorbance detection system shown in FIG. 6.
Figure 9:
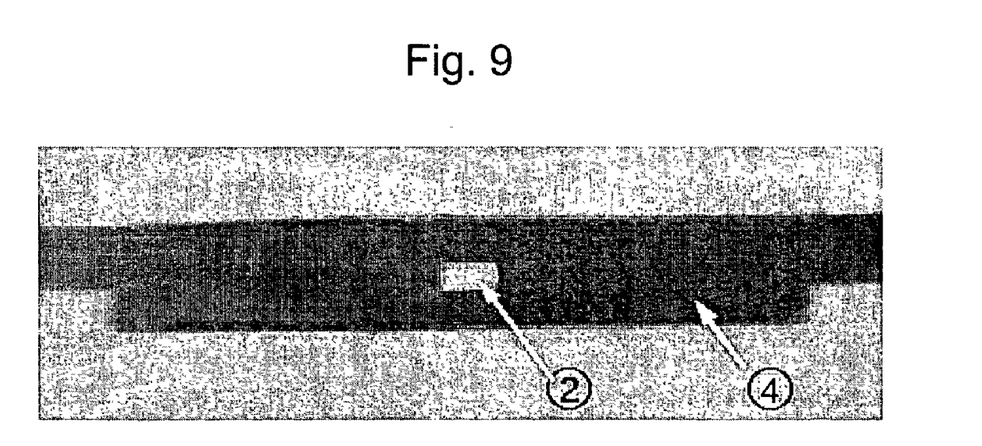
FIG. 9 is a sectional view showing the detection cell surrounded by slits in the absorbance detection system with a collimator according to the present invention.

Light propagation in the detection cells after being emitted through the optical fibers of the absorbance detection systems 100 and 100' fabricated as described with reference to FIGS. 2 through 4 was captured using a charge-coupled device (CCD) camera. The results are shown in FIGS. 6 and 9 for comparison. FIG. 6 shows the absorbance detection system 100' without a collimator (hereinafter, "non-collimated system") near the detection cell 1 before light emission. The source fiber ② having a core diameter of 3 μm is inserted through the source fiber channel 20 (see FIG. 1B or 2), and the collection fiber ③ having a core diameter of 50 μm is inserted through the collection fiber channel 21 (see FIG. 1B or 2). FIG. 7 shows the non-collimated system 100' without a collimator near the detection cell 1 after light emission in which the detection cell 1 is filled with a fluorescent compound (fluorescein) over extended injection time and is irradiated by light from an argon ion laser through the source fiber 2. As shown in FIG. 7, in the non-collimated system 100', light is diverged in the detection cell 1. Evidently, it is hard for all of the light to entirely pass through the detection cell 1.

Figure 8:
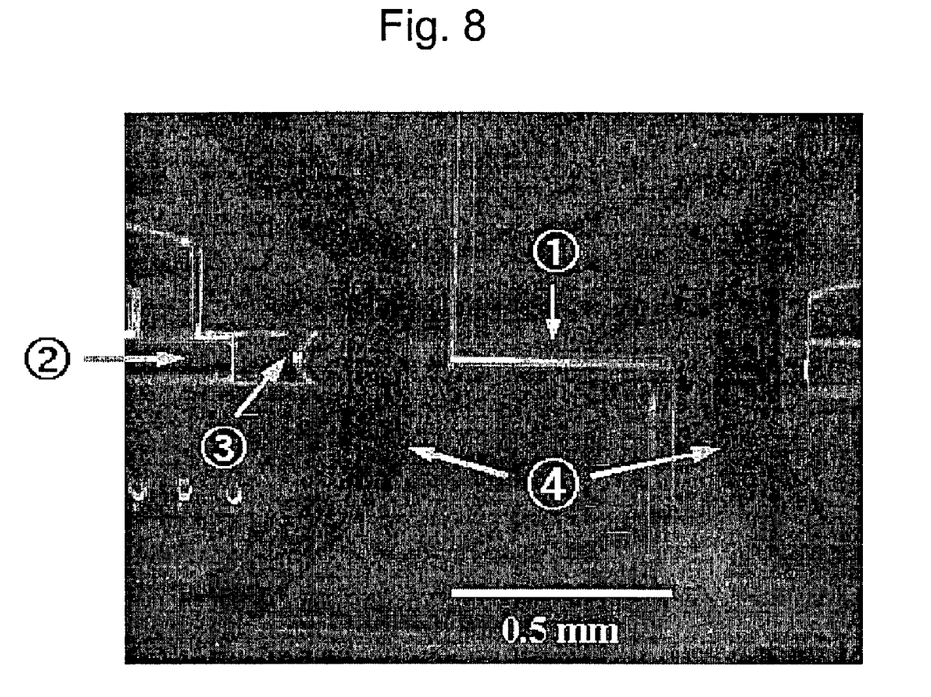
FIG. 8 is a photograph showing collimated light passing through the detection cell in an absorbance detection system with a collimator according to the present invention.

FIG. 8 shows the absorbance detection system 100' with a collimator (hereinafter "collimated system") near the detection cell 1 in which the detection cell 1 is filled with fluorescein and collimated light from the microlens passes through the detection cell 1. Here, the source fiber 2 is arranged at the focal length of the micro-convex lens 3 to obtain collimated light. The slits 4 filled with black ink act as barriers to absorb scattered light. FIG. 9 illustrates a section of the detection cell 1 surrounded by the 3-dimensional slits 4.

The absorption efficiency of the detection cells in the absorption detection systems according to the present invention will be described with reference to FIG. 10.

To determine the absorption efficiency of the collimated and non-collimated detection cells, each of the detection cells is filled with a 5–1500 ppm New coccine solution and irradiated through optical fibers. Next, the intensity of the light passed through each of the detection cells is determined using a photodetector.

Absorbance for a sample solution is calculated by:

$$A = \log(I_0/I)$$

where $I_0$ and I denote the intensity of a signal from a PMT for a detection cell before and after being filled with the solution, respectively. The larger the concentration of solution, the smaller the value of I and the larger the absorbance. According to Beer's law, absorbance of a sample is proportional to its concentration, and thus absorbance of the sample varies linearly with respect to its concentration. When a portion of the incident light improperly passes the detection cell or scattered light enters the detection cell, the range of concentration in which the linearity is satisfied is reduced with a decreased slope.

Figure 10:
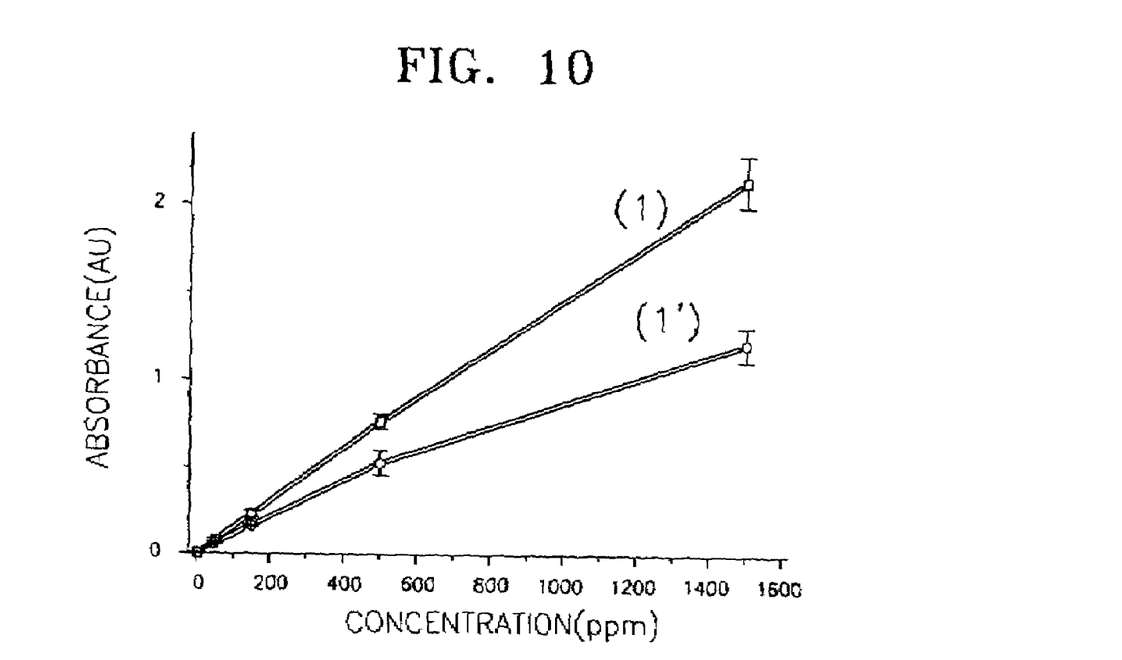
FIG. 10 is a graph comparatively showing absorption efficiency between detection cells of the absorbance detection systems according to the present invention.

FIG. 10 is a graph comparatively showing absorbance with respect to concentration for a collimated detection cell 1 and a non-collimated detection cell 1'. As shown in FIG. 10, the collimated detection cell 1 shows linear absorbance through the entire concentration range, i.e., between 0 and 1500 ppm, whereas the non-collimated detection cell 1' shows linear absorbance up to a concentration of 500 ppm. The absorption efficiency of the collimated detection cell 1 is better than that of the non-collimated detection cell 1'. Also, a reduction in efficiency due to scattered light was not observed in the collimated detection cell 1.

Figure 11:
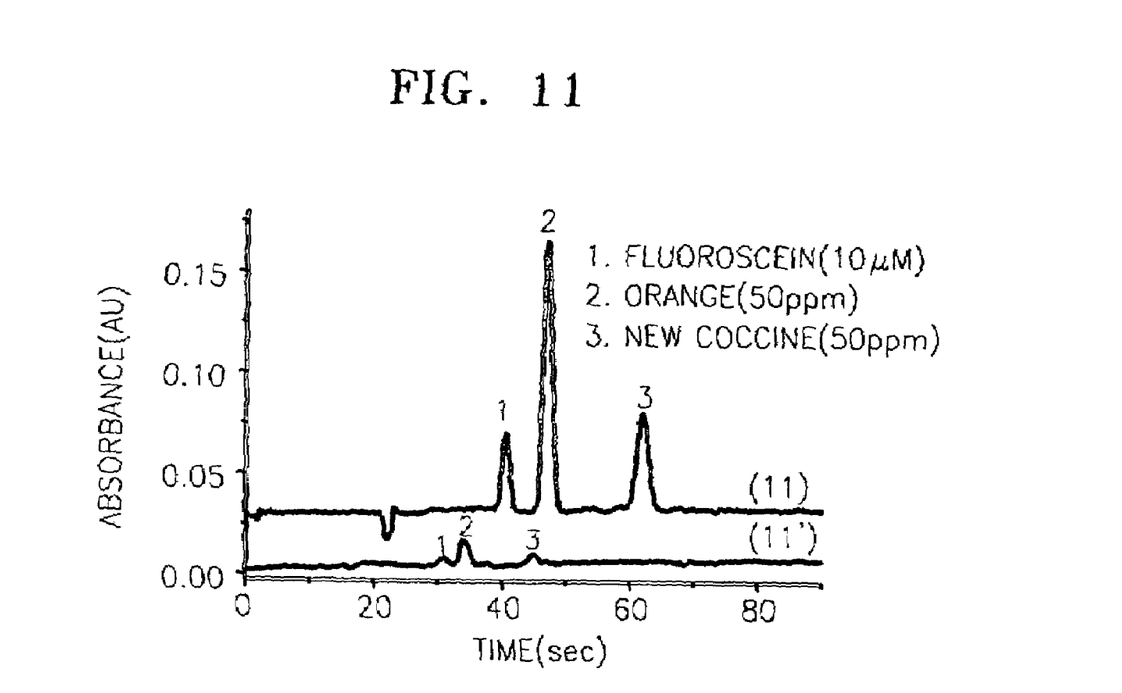
FIG. 11 is a graph comparatively showing detection sensitivity between detection cells of the absorbance detection systems according to the present invention.

Detection sensitivities of the detection cells according to the present invention were compared. The results are shown in FIG. 11. FIG. 11 shows the results of separation of a sample when a non-extended detection cell 11' having an optical pathlength of 50 μm and a collimated detection cell 11 having an optical pathlength of 500 μm are used. The sample used was a mixture of 10 μM of fluoroscein, 50 ppm of Orange II, and 50 ppm of New coccine and was injected for 0.5 seconds.

As shown in FIG. 11, the collimated detection cell 11 shows about 10 times higher sensitivity for each peak than the 50-μm detection cell 11'. Also, the collimated detection cell 11 shows an improved detection limit at 1 to 3 ppm, compared to the detection cell 11' which has a detection limit of 10 to 30 ppm. Separation efficiency is not reduced for the collimated detection cell 11 having such an extended optical pathlength.

As described above, the absorbance detection system in a lab-on-a-chip according to the present invention can be applied for the detection of a variety of samples. The absorbance detection system in a lab-on-a-chip according to the present invention does not need labeling of the samples which saves time and costs compared to a conventional detection method. Therefore, the absorbance detection system in a lab-on-a-chip according to the present invention has high-efficiency and high-sensitivity.

The absorbance detection system in a lab-on-a-chip according to the present invention can be used with wider applications to a variety of samples in diverse research fields, for example, the drug screening field dealing with simultaneous synthesis and identification of a number of substances based on combinatorial chemistry, the life sciences field handling trace bioactive materials such as enzymes, proteins, and amino acids, and the environmental research field which needs rapid field monitoring of contaminants.

The absorbance detection system in a lab-on-a-chip according to the present invention can be used effectively in detecting trace compounds with a much higher sensitivity than a conventional absorbance detection system.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An absorbance detection system in a lab-on-a-chip, comprising:
   a membrane plate sandwiched between two plates;
   a detection cell having an optical pathlength of 50 μm to 5 mm;
   a lens structure with a lens for collimating light in the detection cells; and
   slit structures for preventing scattered light from entering detectors, wherein the detection cell, the lens structure, and the slit structures are disposed on the membrane plate between the two plates.

2. The absorbance detection system of claim 1, wherein the lens for collimating light in the detection cell is selected from the group consisting of a convex lens, a convex-concave compound lens, and a gradient-index(GRIN) lens.

3. The absorbance detection system of claim 1, wherein the slit structures are filled with material capable of absorbing scattered light.

4. The absorbance detection system of claim 3, wherein the material absorbing scattered light is selected from the group consisting of black ink, organic dye solution, and inorganic dye solution.

5. The absorbance detection system of claim 1, wherein the detection cell, the lens structure, and the slit structures comprise the same material as that of the lab-on-a-chip.

6. The absorbance detection system of claim 1, wherein the detection cell, the lens structure, and the slit structures comprise different materials than that of the lab-on-a-chip and are integrated into the lab-on-a-chip.

7. The absorbance detection system of claim 1, wherein the lab-on-a-chip comprises at least one plastic material selected from the group consisting of polydimethylsiloxane (PDMS), polymethylmethacrylate (PMMA), polycarbonate (PC), polyethylene (PE), polypropylene (PP), and polystyrene (PS).

8. The absorbance detection system of claim 1, wherein optical fiber or optical waveguides guide light from a light source to the lens structure and/or from the detection cell to a light detector.

9. The absorbance detection system of claim 1, further comprising a light source for absorbance detection, wherein the light source is a micro-light source selected from the group consisting of a lamp, a light emitting diode and a laser.

10. The absorbance detection system of claim 1, wherein the lens structure and the slit structures comprise collimators supplying collimated light to the detection cells.

11. The absorbance detection system of claim 1, wherein the absorbance detection system in the lab-on-a-chip is fabricated by methods selected from the group consisting of molding, embossing, casting, mechanical machining, and laser machining.

12. The absorbance detection system of claim 2, wherein optical fiber or optical waveguides guide light from a light source to the lens structure and/or from the detection cell to a light detector.

13. The absorbance detection system of claim 5, wherein optical fiber or optical waveguides guide light from a light source to the lens structure and/or from the detection cell to a light detector.

14. The absorbance detection system of claim 6, wherein optical fiber or optical waveguides guide light from a light source to the lens structure and/or from the detection cell to a light detector.

15. A monolithic absorbance detection system comprising:
   opposed top and bottom plates; and
   a membrane plate sandwiched between the top and bottom plates,
      the membrane plate including
         spaced apart source and collection fiber channels at opposed sides of the top and bottom plates for emitting light and receiving light, respectively,
         a detection cell between and spaced from the source and collection fiber channels and through which a fluid sample may flow, and
         a lens structure in the source fiber channel for collimating light entering the source fiber channel and incident on the detection cell,
      the top and bottom plates including
         source and collection fiber channels aligned with the source and collection fiber channels in the membrane plate,
         continuous slit channels spaced from the source and collection fiber channels and the detection cell for receiving an opaque fluid to confine the light entering and leaving the source and collection fiber channels, respectively, thereby preventing scattering of the light.

* * * * *